United States Patent [19]

DeLuca et al.

[11] 4,307,231

[45] Dec. 22, 1981

[54] VITAMIN D-LACTONE DERIVATIVE AND PROCESS FOR PREPARING SAME

[75] Inventors: Hector F. DeLuca; Heinrich K. Schnoes; Yoko Tanaka, all of Madison; Herbert E. Paaren, Verona; Joseph K. Wichmann, Madison, all of Wis.

[73] Assignee: Wisconsin Alumni Research Foundation, Madison, Wis.

[21] Appl. No.: 170,228

[22] Filed: Jul. 18, 1980

[51] Int. Cl.³ .......................................... C07D 307/62
[52] U.S. Cl. .................................. 542/428; 424/279
[58] Field of Search ................................ 542/454, 428

[56] References Cited

PUBLICATIONS

Wichmann et al., J. Biochemistry, vol. 18, pp. 4775 to 4780 (1979).

*Primary Examiner*—John D. Randolph
*Attorney, Agent, or Firm*—Howard W. Bremer

[57] ABSTRACT

The invention provides a new vitamin D compound, 1α,25-dihydroxy-vitamin $D_3$ 26,23-lactone.

The compound is characterized by vitamin D-like activity.

1 Claim, No Drawings

VITAMIN D-LACTONE DERIVATIVE AND PROCESS FOR PREPARING SAME

The invention described herein was made in the course of work under a grant or award from the Department of Health and Human Services.

This invention relates to a novel vitamin D compound.

More specifically, this invention, relates to a lactone derivative of vitamin $D_3$.

The ability of the D vitamins to stimulate intestinal calcium transport, raise serum calcium levels and to enhance the growth of bone is well known and the use of vitamin D as a nutritional supplement is common practice.

It is now also well established that the biological effect of vitamin D depends on metabolism in vivo to hydroxylated forms, and these hydroxy-derivatives of the vitamin are responsible for the physiological functions with which the vitamin is associated. Thus vitamin $D_3$ is first hydroxylated to 25-dihydroxyvitamin $D_3$, considered to be the major circulating metabolite in the bloodstream. This compound is then further hydroxylated in the kidney to produce 24,25-dihydroxyvitamin $D_3$, 25,26-dihydroxyvitamin $D_3$ and 1α,25-dihydroxyvitamin $D_3$. The 1α-hydroxylated form of the vitamin is generally considered the physiologically active form of the vitamin, responsible for what are termed the vitamin D-like activities such as increasing calcium and phosphate absorption, and mobilizing bone mineral. Further, it is a general observation that 1α-hydroxylation of a vitamin D compound tends to enhance its biological activity as compared to the non-1-hydroxylated form. Thus 1α,25-dihydroxyvitamin $D_3$ or 1α,24,25-trihydroxyvitamin $D_3$ are more potent than 25-hydroxyvitamin $D_3$ or 24,25-dihydroxyvitamin $D_3$ in eliciting calcium transport and bone calcium mobilization in vivo and analogs such as 1α-hydroxyvitamin $D_3$ or 1α-hydroxyvitamin $D_2$ are much more potent than the corresponding non-hydroxylated compounds, vitamin $D_3$ and $D_2$ respectively.

Because of their enhanced potency, 1-hydroxylated vitamin D derivatives are highly desirable compounds of potentially broad application as nutritional supplements or as therapeutic agents in clinical practice, and the introduction of novel compounds of this type is therefore of great practical significance. The utility of 1-hydroxylated vitamin D compounds is also illustrated by numerous references to the preparation and use of these derivatives in the patent and other literature, for example, U.S. Pat. No. 3,697,559 directed to 1,25-dihydroxycholecalciferol; No. 3,741,996 directed to 1α-hydroxycholecalciferol; No. 3,847,955 directed to 1,24,25-trihydroxycholecalciferol; No. 3,880,894 directed to 1,25-dihydroxyergocalciferol; No. 3,907,843 directed to 1α-hydroxyergocalciferol.

A new vitamin D compound, possessing the desirable 1α-hydroxy group and an unusual side chain lactone structure has now been found. This compound has been characterized as 1α,25-dihydroxyvitamin $D_3$ 26,23-lactone. This compound therefore represents the 1-hydroxylated analog of 25-hydroxyvitamin $D_3$ 26,23-lactone, a biologically active vitamin D metabolite recently reported by Wichmann et al. (Biochemistry, 18, 4775, 1979); by virtue of the presence of a 1-hydroxy function, the new vitamin D compound of this invention can be expected to exhibit greater biological activity than 25-hydroxyvitamin $D_3$ 26,23-lactone.

PREPARATION AND PURIFICATION

The new vitamin D compound was produced by in vitro hydroxylation of 25-hydroxyvitamin $D_3$ 26,23-lactone using appropriate kidney homogenates. As shown schematically in Process Schematic 1, below, the preparation of 1α,25-dihydroxyvitamin $D_3$ 26,23-lactone (structure II) was achieved by incubation of 25-dihydroxyvitamin $D_3$ 26,23-lactone (structure I) with a kidney homogenate system prepared from vitamin D-deficient chickens.

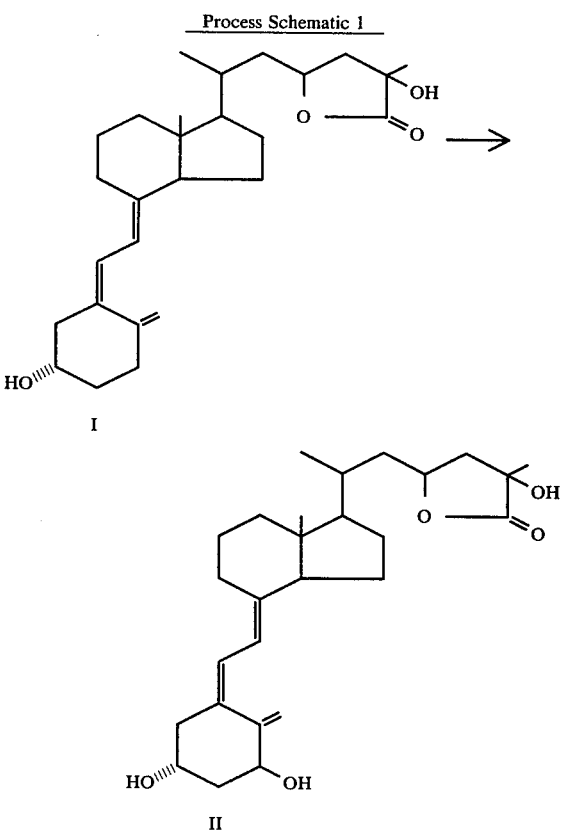

Preparation of 1α,25-dihydroxyvitamin $D_3$ 26,23-lactone (II) from 25-hydroxyvitamin $D_3$ 26,23-lactone (I)

A chick kidney homogenate was prepared as follows: one-day old Leghorn chickens were maintained on the vitamin D-deficient diet described by Omdahl et al. (Biochemistry 10, 2935, 1971) for three weeks. They were then killed by decapitation, their kidneys were removed and a 20% (w/v) homogenate was prepared in ice-cold 0.19 M sucrose, 1.9 mM magnesium acetate and 1.5 mM tris-acetate buffer (trihydroxymethylaminoethane acetate) at pH 7.4.

An aliquot of this homogenate (representing about 600 mg of kidney tissue) was then suspended in an incubation medium consisting of 0.19 M sucrose, 1.9 mM magnesium acetate, 25 mM sodium succinate and 1.5 mM tris-acetate, pH 7.4 (4.5 ml total volume) in a 125 ml Erlenmeyer flask. To this medium was added 10 μg of 25-hydroxyvitamin $D_3$ 26,23-lactone [compound I, Wichmann et al., Biochemistry, 18, 4775 (1979)] dissolved in 50 μl of 95% EtOH. The resulting mixture was incubated for 2 hr at 37° C. under an atmosphere of oxygen in a shaker bath, operating at 100 oscillations per minute. After 2 hr a methanol/chloroform mixture (2:1) was added, the mixture was transferred to a separating funnel and the organic phase was separated. The aqueous phase was extracted once more with the same methanol/chloroform mixture, and the organic extracts were pooled and solvent evaporated. The residue, redissolved in $CHCl_3$/hexane/MeOH (75:23:2), was applied to a Sephadex LH-20 column (1×16 cm), packed and eluted in the same solvent. The first 45 ml of eluant was discarded, the next 80 ml was pooled and solvent was evaporated. The residue was further purified on high-pressure liquid chromatography (HPLC) as follows. The sample was applied onto a silica gel column (Zorbax-Sil, 4.6 mm×25 cm, a product of Dupont Instruments, Wilmington, DE), operated under a pressure of 1,000 psi (ca. 2 ml/min flow rate) in a model ALC/GPC 204 chromatograph (Waters Associates, Medford, MA) equipped with a UV-moniter operating at 254 nm. The column was eluted with 15% 2-propanol in hexane. The desired product (compound II) eluted at 28.5 ml, an elution position just before that of the known vitamin D metabolite 1,24,25-trihydroxyvitamin $D_3$ which elutes at 31 ml in this system. The collected product was then chromatographed on a reversed-phase HPLC system, comprising a Zorbax-ODS column (0.45×25 cm; Zorbax-ODS is a fine-grained silica gel preparation containing chemically bonded octadecylsilane groups; it is a product of Dupont Instruments) and 35% $H_2O$ in MeOH as eluting solvent. The desired product (II) eluting at 17 ml was collected and reapplied to a straight-phase silica gel column (Zorbax-Sil, 0.46×25 cm) and eluted with 15% of 2-propanol in hexane; product II, eluting at 29 ml was collected and subjected to physical characterization.

Characterization of product II as 1α,25-dihydroxyvitamin $D_3$ 26,23-lactone

The product obtained as above was identified as 1α,25-dihydroxyvitamin $D_3$ 26,23-lactone by means of chromatographic and spectral data. Product II, eluted on silica gel HPLC just prior to the known metabolite 1α,24,25-trihydroxyvitamin $D_3$ which was used as a calibration compound for the HPLC system. Since the precursor 25-hydroxyvitamin $D_3$ 26,23-lactone (I) elutes on this same system just before 24,25-dihydroxyvitamin $D_3$, the chromatographic behavior of compound II immediately suggested that it was the 1α-hydroxylated form of precursor I. This was confirmed by mass spectra data, showing a molecular ion at m/e 444, as required for structure II, and peaks due to elimination of $H_2O$ and methyl, namely m/e 426 ($M^+-H_2O$), 411 ($M^+-H_2O-CH_3$) and 408 ($M^+-2\times H_2O$). In addition, the spectrum showed characteristic fragment peaks at m/e 269 ($M^+$-side chain-$H_2O$) and 251 (269—$H_2O$), as well as the ring A fragments at m/e 152 and 134 (152—$H_2O$) which are diagnostic for 1α-hydroxylated vitamin D compounds. The mass spectrum thus presents a pattern analogous to that shown by precursor I (see Wichmann et al, ref. cited) except for the shift of peaks by 16 mass units, reflecting the incorporation of a 1-hydroxy group. Given the fact that the compound is formed from 25-hydroxyvitamin $D_3$ 26,23-lactone, these data prove that product II is the corresponding 1-hydroxylated analog. Further the ratio of the fragments at m/e 152 and 134 (40:100 ) indicates that the 1-hydroxy group has the α-configuration, since it is known (Paaren et al., J. Chem. Soc. Chem. Commun., pp. 890–891, 1977) that 1β-hydroxy configuration results in a very different 152:134 peak ratio (100:90). Hence, the above data establish the product to be 1α,25-dihydroxyvitamin $D_3$ 26,23-lactone, as represented by structure II in Process Schematic 1.

The 1α,25-dihydroxyvitamin $D_3$ 26,23-lactone compound (product II) showed significant binding activity in the intestinal protein receptor binding assay of Eisman et al. [Steroids 30, 245–257 (1977)] and since relative binding affinity in this assay is a measure of the in vivo potency of vitamin D compounds, the novel product of this invention is expected to have utility as a therapeutic agent in disorders of calcium and phosphate metabolism.

Having thus described the invention, what is claimed is:

1. 1α,25-dihydroxyvitamin $D_3$ 26,23-lactone.

* * * * *